(12) United States Patent
Van Der Weij (10) Patent No.: US 11,941,810 B2
(45) Date of Patent: Mar. 26, 2024

(54) MEDICAL IMPLANT INSPECTION USING IMAGING

(71) Applicant: Edwards Lifesciences Corporation, Irvine, CA (US)

(72) Inventor: Hendrik Petrus Van Der Weij, Prangins (CH)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 259 days.

(21) Appl. No.: 17/203,609

(22) Filed: Mar. 16, 2021

(65) Prior Publication Data

US 2021/0224994 A1 Jul. 22, 2021

Related U.S. Application Data

(63) Continuation of application No. PCT/US2019/051556, filed on Sep. 17, 2019.

(60) Provisional application No. 62/733,365, filed on Sep. 19, 2018.

(51) Int. Cl.
  *G06K 9/00* (2022.01)
  *G06T 7/00* (2017.01)
  *G16H 30/40* (2018.01)

(52) U.S. Cl.
  CPC .......... *G06T 7/0014* (2013.01); *G16H 30/40* (2018.01); *G06T 2207/10081* (2013.01); *G06T 2207/20081* (2013.01); *G06T 2207/30048* (2013.01); *G06T 2207/30052* (2013.01)

(58) Field of Classification Search
  CPC ... G06T 7/0004; G06T 7/0006; G06T 7/0008; G06T 7/001; G06T 2207/30108; G06T 2207/30164; G06T 2207/30052; G06T 2207/10081; G06T 7/0012–0016; G06T 2207/10064–10136; G06T 2207/30004–30104; G06T 2207/20081; G06T 2207/20084; G05B 2219/45172; A61F 2/24–2496; G06V 2201/031; G06V 2201/03–034; G06V 10/70; G06V 10/82; G06V 10/774–7796; G06K 9/6256; G06K 9/6257; G06K 9/6259; G06N 3/02–126; G06N 20/00–20; G06F 18/214–2155; G06F 7/023; G06F 40/16; G01N 23/00; G01N 23/046
  See application file for complete search history.

(56) References Cited

U.S. PATENT DOCUMENTS 6,453,062 B1 * 9/2002 MacNutt ................. G06T 7/001
  382/128
10,217,237 B1 * 2/2019 Goncharov ............... B21F 1/00
(Continued)

FOREIGN PATENT DOCUMENTS

EP          0277694 A2 * 10/1998 ............. G01N 33/36
WO   WO-2019107614 A1 * 6/2019 ........... G06K 9/3233

*Primary Examiner* — Atiba O Fitzpatrick
(74) *Attorney, Agent, or Firm* — Alan T. Hale; CHANG AND HALE LLP (57) ABSTRACT

An apparatus for inspecting a target device includes a data communication interface and control circuitry configured to receive imaging data of a target device using the data communication interface, determine image features associated with the target device based at least in part on the imaging data, and determine an inspection outcome based at least in part on the image features.

16 Claims, 5 Drawing Sheets

(56) References Cited

U.S. PATENT DOCUMENTS

| | | | | |
|---|---|---|---|---|
| 2014/0003695 | A1* | 1/2014 | Dean | A61B 5/1075 |
| | | | | 382/131 |
| 2016/0007967 | A1* | 1/2016 | Johnson | A61F 2/0105 |
| | | | | 600/458 |
| 2018/0113083 | A1* | 4/2018 | Van Dael | G01N 23/046 |
| 2018/0374022 | A1* | 12/2018 | Wang | G06N 20/00 |
| 2018/0374207 | A1* | 12/2018 | Niculescu-Mizil | G06F 18/211 |
| 2018/0374569 | A1* | 12/2018 | Niculescu-Mizil | G06F 18/214 |
| 2019/0325570 | A1* | 10/2019 | Wenzel | G01N 23/046 |
| 2019/0378261 | A1* | 12/2019 | Schultz | G06T 7/254 |
| 2020/0027374 | A1* | 1/2020 | Stone | G09B 19/24 |
| 2021/0063323 | A1* | 3/2021 | Nakatani | G01N 23/18 |
| 2021/0229362 | A1* | 7/2021 | Kofidis | A61F 2/2418 |

\* cited by examiner

MEDICAL IMPLANT INSPECTION USING IMAGING

RELATED APPLICATIONS

This application is a continuation of International Patent Application No. PCT/US2019/051556, filed Sep. 17, 2019, which claims the benefit of U.S. Patent Application No. 62/733,365, filed Sep. 19, 2018, the entire disclosures all of which are hereby incorporated by reference for all purposes.

BACKGROUND

Field

The present disclosure generally relates to the field of implant device manufacturing and inspection, and associated systems, devices, and methods.

Description of Related Art

Manufacturing prosthetic heart valves and other human prosthetic implant devices may involve quality inspections to identify defects in manufactured products and/or make product rejection determinations. The use of manual handling and inspection by humans for quality inspection and product rejection determination can be random, costly and time consuming.

SUMMARY

In some implementations, the present disclosure relates to an apparatus for inspecting a target device. The apparatus comprises a data communication interface, and control circuitry configured to receive imaging data of a target device using the data communication interface, determine image features associated with the target device based at least in part on the imaging data, and determine an inspection outcome based at least in part on the image features.

The imaging data may comprise three-dimensional computed tomography imaging data. In some embodiments, the target device is a prosthetic heart valve device. The image features may include features relating to one or more of contaminant presence, dimensions, color, and shape associated with one or more portions of the target device. In some embodiments, the control circuitry is further configured to determine the inspection outcome based at least in part on a failure prediction model. For example, the control circuitry may be further configured to obtain a set of image feature data associated with a plurality of reference devices, obtain inspection decision data corresponding to the plurality of reference devices, the inspection decision data including failure decision data, determine correlations between the failure decision data and the set of imaging feature data, and determine the failure prediction model based on the correlations.

In some embodiments, the inspection outcome is a failure determination, and the control circuitry is further configured to send a command to a device remover device to remove the target device from a manufacturing process flow based on the failure determination.

In some implementations, the present disclosure relates to a method of generating an inspection prediction model. The method comprises obtaining imaging data for a plurality of reference devices, determining image features associated with the imaging data, obtaining inspection decision data associated with the plurality of reference devices, determining correlations between the image features and the inspection decision data, and generating an inspection prediction model based at least in part on the correlations.

The inspection decision data may indicate human inspection results for each of the plurality of reference devices. In some embodiments, the inspection prediction model is a polynomial model having one or more variable associated with the image features. The inspection prediction model may be based at least in part on product specification data associated with the plurality of reference devices. The method may further comprise generating the imaging data for the plurality of reference devices.

In some implementations, the present disclosure relates to a method of determining an inspection decision for a target device. The method comprises obtaining imaging data for a target device, determining image feature data of the imaging data, evaluating the image feature data using an inspection prediction model, and determining an inspection outcome associated with the target device based on the evaluation.

The imaging data may comprise computed tomography imaging data. In some embodiments, the target device is a prosthetic medical implant device. The image feature data can include one or more of contaminant presence data, dimensions data, color data, and shape data. In some embodiments, determining the inspection outcome is based at least in part on a failure prediction model. For example, the method may further comprise obtaining a set of image feature data associated with a plurality of reference devices, obtaining inspection decision data corresponding to the plurality of reference devices, the inspection decision data including failure decision data, and generating a failure prediction model based on correlations between the failure decision data and the set of imaging feature data. In some embodiments, the method further comprises removing the target device from a process flow based on the inspection outcome.

In some implementations, the present disclosure relates to a device inspection system comprising an imaging device, and one or more non-volatile data storage devices storing image feature data associated with a plurality of reference devices, and inspection decision data associated with the plurality of reference devices. The device inspection system further comprises control circuitry configured to access the image feature data and the inspection decision data, to generate a failure prediction model based on correlations between features indicated by the image feature data and failure determinations indicated by the inspection decision data, to receive imaging data for a target device from the imaging device, and to determine an inspection outcome associated with the target device based at least in part on the failure prediction model and one or more features indicated by the imaging data for the target device. The system can further comprise a conveyor device configured to advance the target device through a scanning region of the imaging device.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order-dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Prosthetic heart valve implants, as well as many other types of prosthetic implant devices and non-implant devices, can include various welded, connected, sutured, positioned, and/or attached components and/or portions. The manufacturing and assembly of such devices can result in the occurrence or introduction of defects or contaminants associated with one or more components of the device(s), which, in certain instances, can result in failure of the device to pass quality inspection. That is, certain defects or contaminants in a medical device may result in the device being unsuitable for use in its present condition, or such defects or contaminants may indicate that additional corrective measures should be taken with respect to the defective device. In some implementations, manual human inspection of medical implant devices, or other types of devices, is performed on a one-by-one basis, wherein each individual product being inspected may need to be physically handled and inspected by the inspector. It should be understood that description of inspection of devices in the present disclosure may be performed at least in part by either an operator inspector or a device assembler, or both. Therefore, the term "inspector" is used herein according to its broad and ordinary meaning, and includes operators and/or assemblers, or other inspector individuals or entities.

The present disclosure relates to systems, devices, and methods for inspecting medical implant devices, and/or other types of apparatuses or devices, and providing failure decisions related thereto. The term "failure" is used here and according to its broad and/ordinary meaning, and may refer to any status, state, condition, or the like of a device, such as medical device, wherein such status, state, condition, or the like, is of a nature such that the device is deemed presently unsatisfactory for production or advancement in a manufacturing and/or evaluation process. For example, failure decisions in accordance with the present disclosure may relate to visual defects, such as stains, or other visual defects that may or may not hinder or affect function of the subject device in a substantial way. Failure decisions may further relate to assembly errors, or any other type of error or condition of a device, or component thereof, that may affect the suitability of the device for use and/or production. The terms "failure determination," "failure evaluation," "failure decision," "fail determination," "negative pass/fail determination," "rejection determination," "rejection evaluation," and the like, are used herein to describe a negative inspection outcome or determination, which may lead to disposal of the subject device, removal of the device from a process (e.g., manufacturing process) flow, remedial action to at least partially correct a defective condition, or other responsive action. Furthermore, such terms may refer to the determination process for determining whether a target device passes or fails a quality inspection. The terms "pass/fail determination" and "pass/fail decision" may refer to a determination regarding whether a target device meets or does not meet certain quality inspection criteria. Rejection or failure determinations may result from the identification of a defective condition in the subject device, such as the presence of contaminant(s), or defective connections or configurations of one or more components thereof. The terms "subject device," "target device," and "product" are used herein according to their broad and ordinary meanings, and may refer to a device, such as a heart valve device or other prosthetic implant device, that is under quality inspection or otherwise subject to quality inspection or evaluation.

Devices inspected in accordance with principles disclosed herein can include any type of medical implant device, such as, for example, prosthetic heart valve devices. For example, heart valve devices that may be inspected in accordance with the present disclosure may include transcatheter heart valves (THVs), surgical heart valves (e.g., replacement aortic or mitral valve devices), annuloplasty rings (e.g., mitral or tricuspid annuloplasty devices), or other devices. During a manufacturing process, such devices can present failures or defects that do not allow for the device to pass quality inspection according to certain relevant inspection parameters or criteria. Certain exemplary medical implant devices are described below as examples of devices that may be subject to quality inspection and/or failure determinations in accordance with the present disclosure. Such devices are described as example devices for convenience and to provide context to certain aspects of the present disclosure, and it should be understood that the principles disclosed herein may be applicable to other types of implant devices, or other apparatuses or devices that may be evaluated or inspected to identify defects or features associated therewith.

Example Inspection of Prosthetic Implant Devices

Devices that may be the subject of quality inspection include prosthetic heart valve implant devices. Generally, the human heart includes four valves for aiding the circulation of blood therein, including the tricuspid valve, which separates the right atrium from the right ventricle; the pulmonary valve, which separates the right ventricle from the pulmonary artery; the mitral valve, which separates the left atrium from the left ventricle; and the aortic valve, which separates the left ventricle from the aorta. Heart valves may generally comprise a relatively dense fibrous ring, referred to herein as the annulus, as well as a plurality of leaflets attached to the annulus. Generally, the size of the leaflets may be such that when the heart contracts, the resulting increased blood pressure produced within the corresponding heart chamber forces the leaflets at least partially open to allow flow from the heart chamber. As the pressure in the heart chamber subsides, the pressure in the subsequent chamber or blood vessel may become dominant, and press back against the leaflets. As a result, the leaflets come in apposition to each other, thereby closing the flow passage. The tricuspid valve comprises three leaflets, and may generally close during ventricular contraction (e.g., systole) and open during ventricular expansion (e.g., diastole). The pulmonary valve comprises three leaflets, and is generally configured to open during systole so that blood may be pumped toward the lungs, and close during diastole to prevent blood from leaking back into the heart from the pulmonary artery. The mitral valve comprises two leaflets, and may generally be configured to open during diastole so that blood in the left atrium can flow into the left ventricle, and close during diastole to prevent blood from leaking back into the left atrium. The aortic valve comprises three leaflets, and is generally configured to open during systole to allow blood leaving the left ventricle to enter the aorta, and close during diastole to prevent blood from leaking back into the left ventricle.

Figures 1, 2, 3:
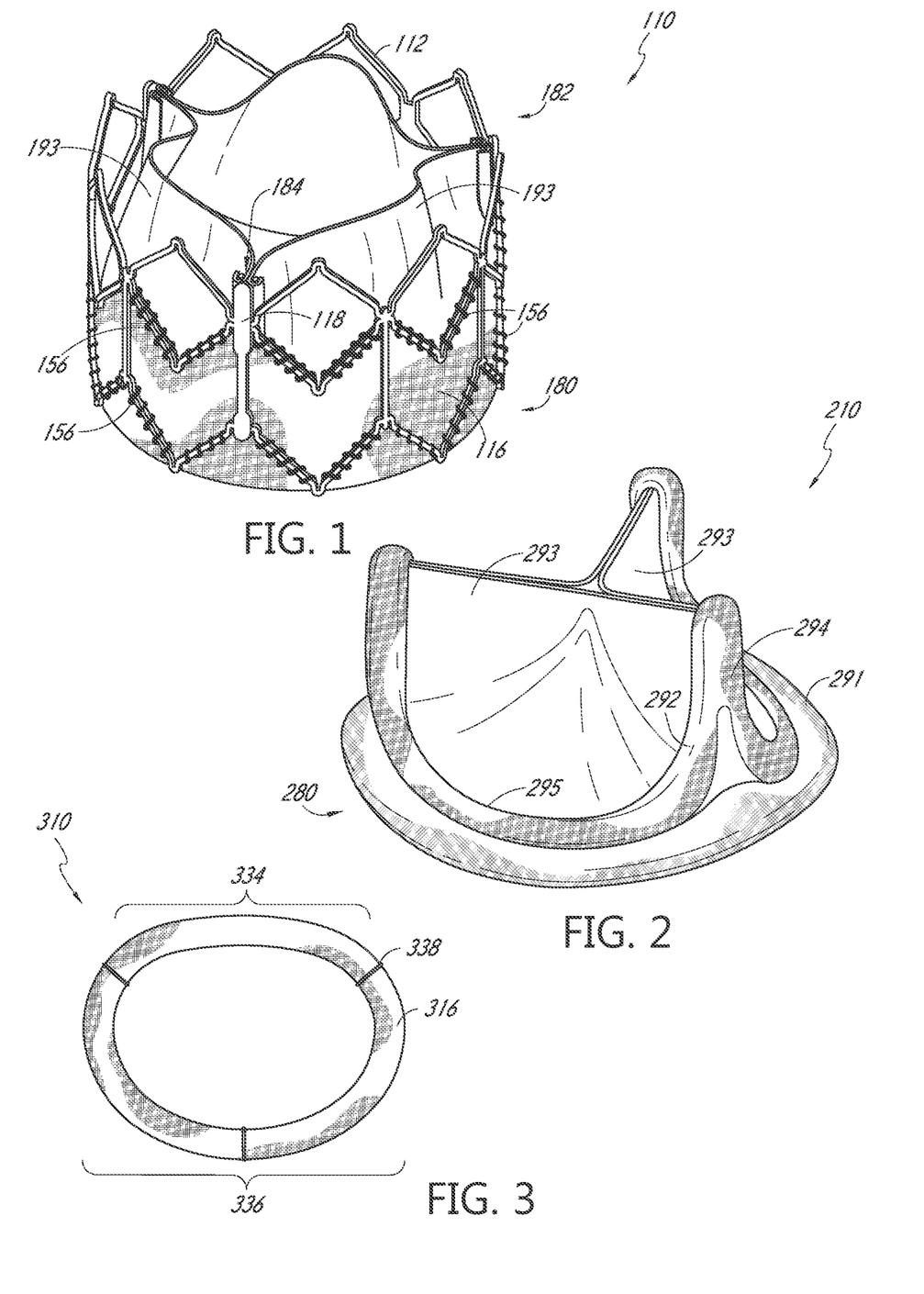
FIG. 1 is a perspective view of a transcatheter heart valve in accordance with one or more embodiments.
FIG. 2 is a perspective view of a surgical heart valve in accordance with one or more embodiments.
FIG. 3 is a top view of an annuloplasty ring in accordance with one or more embodiments.

As referenced above, inspection and/or failure determinations in accordance with embodiments the present disclosure may be implemented in connection with transcatheter heart valve devices. FIG. 1 is a perspective view of a transcatheter heart valve 110 in accordance with one or more embodiments. The features of the valve 110 described herein can apply to other valves, including other valves described elsewhere herein. The valve 110 can be, for example, a self-expanding heart valve, a balloon-expandable heart valve, and/or mechanically-expandable heart valve. The valve 110 in the illustrated embodiment can generally comprise a frame, or stent, 112, a leaflet structure 193 supported by the frame 112, and a sealing member or skirt 116 secured (e.g., sutured) to at least a portion of the frame 112 and/or portion of the leaflet structure 193. In certain embodiments, the valve 110 may be configured to be implanted in the annulus of a native heart valve of a human, such as an aortic valve. However, the valve 110 can additionally or alternatively be adapted to be implanted in other native valves of the heart, or in various other vasculature, ducts, or orifices of the body, or in grafts, docking stents, docking stations, rings, or the like, implanted in the body. The lower end 180 of the valve 110, according to the illustrated orientation, may represent an inflow end, while the upper end 182 of the valve 110, according to the illustrated orientation, may represent an outflow end.

The valve 110 and the frame 112 may be configured to be radially collapsible to a collapsed or crimped state/configuration for introduction into the body using a delivery catheter, and further may be configured to be radially expandable to an expanded state/configuration for implanting the valve at a desired location in the body (e.g., the native aortic valve). In certain embodiments, the frame 112 may comprise a plastic, polymer, shape memory material, or mechanically expandable material that permits crimping of the valve 110 to a smaller profile for delivery and expansion of the valve. In some embodiments, an expansion device, such as the balloon of a balloon catheter or a tool for mechanical expansion, may be used to directly or indirectly expand the valve. In certain embodiments, the valve 110 may be a self-expanding valve, wherein the frame is made of a self-expanding material such as a shape memory material or metal (e.g., nitinol). Self-expanding valves may be able to be crimped to a smaller profile and held in the crimped state with a restraining device, such as a sheath covering the valve. When the valve is positioned at or near the target site, the restraining device may be removed or retracted to allow the valve to self-expand to its expanded, functional size or to a deployed configuration.

The sealing portion or skirt 116 may comprise a single piece or multiple pieces or material (e.g., cloth, polymer, etc.) with opposite ends that are secured to each other to form the annular shape shown in FIG. 1 or extend around a circumference of the valve. In certain embodiments, the upper edge of the sealing portion or skirt 116 can have an undulating shape that generally follows the shape of struts of the frame 112. In this manner, the upper edge portions of the sealing portion or skirt 116 can be tightly secured to respective struts with sutures 156. The sealing portion or skirt 116 may be placed on the outside of the frame 112 or on the inside of the frame 112 (as shown) and an upper edge portion of the sealing portion or skirt 116 may be wrapped around the upper surfaces of the frame struts and secured in place with sutures. The sutures 156 may serve to provide a durable attachment of the sealing portion or skirt 116 to the frame 112.

The leaflet structure 193 can comprise three leaflets (as shown in FIG. 1) in certain embodiments, which can be arranged to collapse in a tricuspid arrangement. Although a three-leaflet embodiment is illustrated, it should be understood that valve implants inspected and/or evaluated according to embodiments disclosed herein may have any number of leaflets, such as, for example, two or four. The leaflets 193 may be formed from separate flaps of material or tissue, such as, for example, xenograft tissue (e.g., bovine pericardium), or all three leaflets can be derived from a single xenograft valve (e.g., a porcine valve). The lower edge of leaflet structure 193 may have a variety of shapes. In certain embodiments, the lower edge of the leaflet structure 193 may have an undulating, curved, and/or scalloped shape that may be sutured to the frame 112. The leaflets 193 can be secured to one another at their adjacent sides to form commissures 184 of the leaflet structure, where the edges of the leaflets come together. The leaflet structure 193 can be secured to the frame 112 using any suitable techniques and/or mechanisms. For example, the commissures 184 of the leaflet structure may be aligned with the support posts 118 and secured thereto, such as by using sutures, adhesive, clamping portions, crimping, and/or other attachment means. In one embodiment, the point of attachment of the leaflets 193 to the posts 118 can be reinforced, e.g., with bars comprising a relatively rigid material, such as stainless steel. Any of the various points of attachment of the valve 110 may be inspected for defects in a quality inspection in accordance with aspects of the present disclosure.

In some embodiments, a lower edge portion (not shown) of the skirt 116 is configured to fold upward over the frame 112 from below the bottom portion of the frame, and sutured thereto. The folded-over portion of the skirt may be sutured to respective struts of the frame 116. Folding-over and securing the skirt 116 to the frame from the outside can allow for excess material to fill in gaps between the frame 116 and the surrounding native annulus to assist in forming a fluid-tight seal between the valve and the native annulus. Such a configuration may at least partially prevent perivalvular leakage after implantation of the valve.

Quality inspection of the valve device 110 may involve assessment or evaluation of the various points of attachment between the leaflets and the posts 118 and/or stent/frame 112. Furthermore, inspection may involve evaluation of the various sutures executed to attach the leaflets 193, frame 112, and/or other components of the valve 110 to one another. Furthermore, inspection of the valve 110 may involve identifying the presence of foreign particulates, or other contaminants, in various regions of the valve 110, such as in folds or wedges thereof. The quality of the leaflet tissue or material 193 may also be evaluated as part of quality inspection, such as to identify areas of delamination in the leaflets.

FIG. 2 is a perspective view of a prosthetic human heart valve 210 in accordance with one or more embodiments. The heart valve 210 may be considered an embodiment of a surgical prosthetic heart valve. The heart valve 210 may include a peripheral sealing ring structure 291 configured to provide support for nesting the heart valve 210 in a heart valve cavity and/or resting upon, or being attached to, a native valve annulus or other structure of the heart. The valve 210 can further include a frame member 292, such as a metal and/or plastic frame, which may provide support for a plurality of flexible leaflets 293 and can define three (or two) upstanding commissure posts 294, wherein the leaflets 293 can be supported between the commissure posts 294. In one embodiment, as shown in FIG. 2, the sealing ring 291 can attach around the periphery of the frame member 292 at the inflow end 280 of the valve 210, with the commissure posts 294 projecting in the outflow direction.

The leaflets 293 may be formed from separate flaps of material or tissue, such as, for example, xenograft tissue (e.g., bovine pericardium), or all three leaflets can be derived from a single xenograft valve (e.g., a porcine valve). The leaflets 293 can be secured and supported both by the commissure posts 294, as well as along arcuate cusps 295 of the frame member between the commissure posts. Similarly to the prosthetic heart valve 110 of FIG. 1, the prosthetic heart valve 210 has a valve orifice (not shown) on the inflow end 280 of the valve through which blood may flow in one direction, but the valve leaflets 293 substantially prevent blood flow in the opposite direction.

One or more components of the heart valve 210 may be covered with cloth, as shown. The covering of the valve 210 with cloth may involve the bringing together of cloth portions to form joints or seams, which may be completed by suturing, or other well-known cloth-edge joining techniques. The cloth can be wrapped around the frame 292, as shown. Cloth covers can be formed of any biocompatible fabric, such as, for example, polyethylene terephthalate. The suturing of the cloth to the frame and/or other components, when improperly executed, can serve as a basis for rejecting the heart valve during a quality inspection. In some implementations or situations, it may not be possible or practical for certain defects and/or areas or components of a device to be inspected manually after the cloth has been sutured to the frame and/or other components.

FIG. 3 shows an embodiment of an annuloplasty ring 310 according to one or more embodiments. The annuloplasty ring 310 can be used for the repair of a native heart valve. For example, the annuloplasty ring 310 can provide a surgical device that can be used for the repair of leaking valves, such as for example, mitral or tricuspid valves. As described above, due to various factors, the leaflets that normally seal a natural valve to retrograde flow may not coapt properly in some cases. Surgical repair of such valves can involve the implantation of an annuloplasty ring to reshape the native valve annulus, wherein the annuloplasty ring, as implanted, may be configured to pull the leaflets together to facilitate coaptation and help to re-establish the proper native valve function.

The annuloplasty ring 310 can have an oval or somewhat D-shaped configuration with a relatively straight anterior section 334 opposite a relatively curved posterior section 336. The annuloplasty ring 310 further comprises a cloth covering 316, which may be stitched over or otherwise disposed over an inner frame of the annuloplasty ring (not shown). The annuloplasty ring 310 may further comprise one or more seams, stitches, or other features 338 associated with the cloth covering 316, which may serve as commissure and/or trigone markers in some embodiments. The shaped posterior section 336 may be shaped to generally follow the shape of a mitral annulus. For example, the posterior section 336 may be at least partially bowed downward (e.g., into the page with respect to the illustrated orientation) relative to the anterior section 334. Alternatively, the annuloplasty ring 310 may have a substantially planar configuration. Some tricuspid rings include multiple tortuosities. Generally, the inspection of three-dimensionally-shaped elements, such as components of prosthetic valves and annuloplasty rings, can be relatively complex. For example, two-dimensional imaging technology may not provide sufficient information for inspecting three-dimensionally-shaped elements in some situations.

Annuloplasty rings like that shown in FIG. 3 may be subject to quality inspections at various stages of a manufacturing. Quality inspection may be implemented to identify defective shape, or incorrect or unsatisfactory stitch work, among other aspects. In addition to prosthetic heart valves and annuloplasty rings, examples of which are described above, quality inspection may be performed on delivery catheters and/or systems for delivering medical implant devices, such as heart valve devices, to a target site, as well as sub-components and/or accessories for such devices, including sizers, holders, crimpers, etc.

Figure 4:
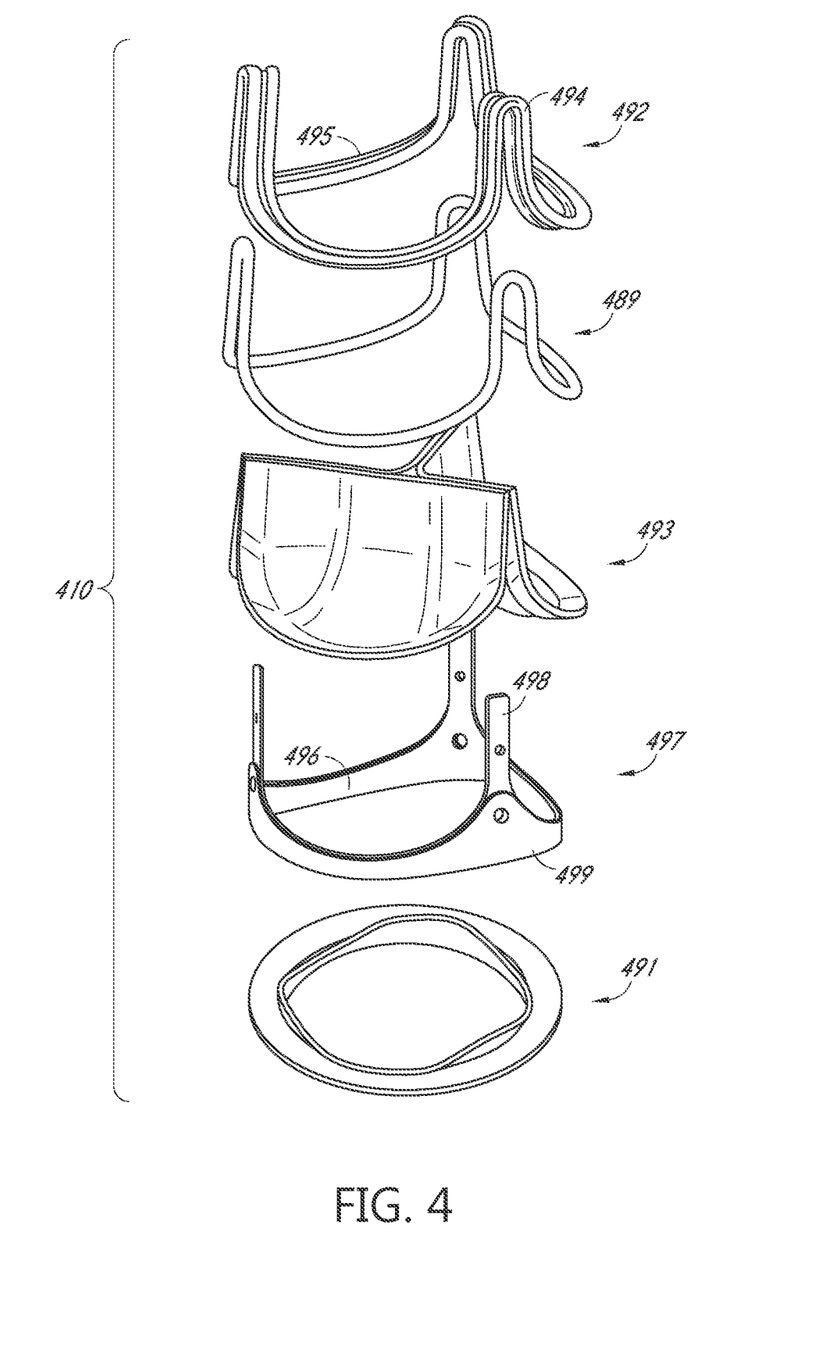
FIG. 4 is an exploded perspective view of a prosthetic heart valve in accordance with one or more embodiments.

With further reference to prosthetic heart valve devices, such devices may comprise various components, the assembly of which may result in certain defects that justify an inspection failure determination. For example, FIG. 4 shows an exploded perspective view of a prosthetic heart valve 410, which may be similar in certain respects to the surgical heart valve 210 of FIG. 2. Although a surgical valve is shown in FIG. 4, it should be understood that transcatheter heart valves, annuloplasty rings, and other medical implant devices may likewise comprise an assembly of a plurality of separate components, the attachment/assembly of which may result in the introduction of various defects, and therefore, the description below relating to FIG. 4 is applicable to assembly of other types of prosthetic implant devices.

The valve assembly 410 includes a frame member 489, which can comprise a metal or other at least partially rigid frame structure, for example, a wireform 489. In certain embodiments, the frame member 489 can be at least partially covered with fabric 492 or other material. The frame 489 and fabric 492 assembly can define relatively narrow arcuate upwardly-projecting commissure regions 494 in-between downwardly-projecting arcuate cusps 495. The valve assembly 410 can further include a stent member 497 designed to fit above a sealing ring 491. In certain embodiments, the stent member 497 includes a plastic band 496 (e.g., polyester, polyethylene terephthalate (PET), or biaxially-oriented PET, for example, Mylar BoPET, DuPont Teijin Films, Wilmington, Delaware), which can also be covered with cloth.

The frame 489 and stent member 497 can be at least partially secured or attached to a leaflet assembly 493, for example, by sandwiching the leaflet assembly therebetween, and sewing through the fabric cover of the frame, the leaflet assembly, and the fabric cover of the stent member. Attachment to the frame 489 can damage the leaflets 493, such as tearing thereto, or improper attachment of the leaflets 493 can result in a failed quality inspection. The leaflets 493 can be made of any suitable material that provides flexibility and structure for occluding fluid flow through the valve 410, as described above, for example, at least in part, biologically-derived tissue. As assembled, the leaflets 493 extend inward from the surrounding frame 492 into a flow orifice defined thereby. In certain embodiments, there are three bio-prosthetic leaflets that curve toward the outflow direction and coapt in the middle of the valve orifice to facilitate one-way flow through the valve. Improper coaptation of the leaflets 493 may serve as a basis for failure of quality inspection.

The valve assembly 410 further includes a stent member 497 designed to fit above a sealing ring 491. In certain embodiments, the stent member 497 includes a plastic band 496 (e.g., polyester, polyethylene terephthalate (PET) (for example, DACRON® PET, Invista, Wilmington, Delaware), or biaxially-oriented PET (for example, MYLAR® BoPET), wherein the leaflets 493 can be sewn or otherwise attached to the plastic band. Incorrect stitching of the leaflets 493 to the stent member 497 may be identified during quality inspection, and may serve as a basis for a failure determination. Therefore, visibility and identification of stitches coupled to the stent member 497 and/or leaflets 493 can be helpful for quality evaluation of the device assembly 410. The stent member 497 can further include a rigid stiffening band 499, which can comprise, for example, metal or other rigid material. The plastic band 496 can include a commissure support portion 498, which can fit at least partially within the upwardly-projecting commissure regions 494 of the frame member 492. Proper coupling of the stent member 497 to the frame member 492 can be confirmed during quality inspection, and improper coupling, or damage associated therewith, can serve as a basis for a failure determination.

The sealing ring 491 of the heart valve assembly 410 can be configured to at least partially stabilize the annulus and/or to support the functional changes that occur during the cardiac cycle, such as by maintaining coaptation and valve integrity to prevent reverse flow while permitting good hemodynamics during forward flow. The sealing ring 491 can comprise an inner at least partially rigid substrate (e.g., metal such as stainless or titanium, or a flexible material such as silicone rubber, fabric (e.g., REEMAY® non-woven polyester fabric, Fiberweb, Wilmington, Delaware), or cordage (e.g., DACRON® PET cordage), and can be at least partially covered with a biocompatible fabric or cloth (not shown) to allow the ring to be sutured to the heart tissue. The sealing ring 491 can be stiff or flexible, and can have a variety of shapes, including circular, D-shaped, kidney-shaped, or C-shaped. In some embodiments, the heart valve 410 can include various visualization markers (not shown; e.g., radiopaque markers and/or visual markers), which can aid in quality inspection.

When coupling or suturing the various components of the valve assembly 410 shown in FIG. 4, certain particles, debris, or other contaminants (e.g., oils) may attach to one or more components, or may become lodged between coupled components or regions. The presence of such particles or other contaminants can negatively affect the performance of the heart valve, and/or may result in injury to the patient recipient of the valve implant. Therefore, quality inspection processes and mechanisms may advantageously provide visibility or indications for identifying such particles, debris, or other contaminants, and the presence of such contaminants may serve as a basis for a failure determination in a quality inspection. In some situations, visibility of particles, debris, or other contaminant(s) may require use of one or more image-enhancement tools, such as microscopes, cameras, or the like. Furthermore, manual inspection techniques, as described above, may result in damage to component(s) of a device being inspected. For example, manual manipulation of heart valve leaflets can result in damage and/or an increased risk of failure/rejection of the device during inspection. Although certain embodiments are described herein in the context of heart valve devices, it should be understood that such description is applicable to other types of prosthetic implant devices, as well as certain non-biological applications.

Device Inspection/Evaluation

As referenced above, quality inspection of medical implant devices and other devices and apparatuses may be performed in a variety of ways. For example, inspection of devices may be implemented through manual inspection by one or more human inspectors of a device at one or more stages of manufacturing or assembly. With regard to manual inspection processes, due to the relatively high dependency on inspector judgment, such processes can involve a risk of inconsistency in outcomes with respect to different inspectors. That is, although different inspectors may inspect devices according to certain parameters or criteria, in execution, subjective judgments of such inspectors in applying such parameters or criteria may result in inconsistency in determined outcomes by such operators. Furthermore, manual visual inspection by a human inspector can be relatively time-consuming and/or costly, and can increase the risk of damage to the subject device, thereby resulting in an increased risk of inspection failure. Furthermore, where failure determinations are made by a review board of engineers, trainers, and/or supervisors to determine whether an identified product is in a failure state and should be disposed of or subject to corrective process(es), such additional review can likewise be undesirably or prohibitively costly in some situations. Furthermore, additional review of a device may increase the risks of damage and/or failure thereof.

Manual human inspection of medical implant devices can involve the use of one or more microscopes or other visual aids or enhancement tools to identify relatively small defects or conditions that may serve as a basis for product rejection. For example, with respect to prosthetic heart valves, visual aids or enhancement tools may be used to help identify tissue damages with respect to valve leaflets or other components, particles that have become stuck, lodged or otherwise undesirably disposed somewhere on or in the heart valve, or sutures or threads that may have been incorrectly sewn or omitted. Furthermore, with respect to heart valve devices, a frame component thereof may not be properly welded or closed, which may likewise represent a condition that may serve as the basis for rejecting the heart valve at one or more stages of the manufacturing process. Any of a variety of defective conditions, as described herein, may result in the subject product being judged to be rejected.

With respect to heart valve devices incorporating biological tissue, such as for valve leaflets or the like, it may be necessary or desirable for such components of the heart valve devices to be maintained in a relatively moist state in order to prevent the tissue thereof from becoming undesirably dehydrated or dried-out, which may result in cracking, breaking, or other damage to the biological tissue. Therefore, in some implementations, a heart valve being inspected is maintained in a jar or other container having fluid or other moisturizing element contained therein, wherein the human inspector may be required to physically remove the valve device from the container for inspection. The inspector may then use a microscope or other visual enhancement tool to inspect the withdrawn device. However, during periods of time during which the valve is removed from the moisture-maintaining container, it may be necessary or desirable for the inspector to soak or spray one or more components of the valve in a moisturizing fluid or gas in order to maintain the desired or necessary moisture in the biological tissue of the heart valve device. In some implementations, re-soaking of the valve being inspected must be performed every minute, or other period of time that the device is exposed outside of the container. Once inspection is complete, the prosthetic valve device may be returned to the container, and the container may be closed to retain moisture therein and/or otherwise to protect the device from contamination or damage. The inspector may then fill out certain paperwork or provide other input indicating that the inspection of the device has been completed. If a defect or error in the inspected devices is observed, the inspector may identify such defect/error in some manner, at which point a final disposition may be prepared with respect to the inspected product.

Inspection of medical implant devices, such as prosthetic heart valve devices, may be performed at various stages in the manufacturing/assembly process. For example, a device may be inspected when biological tissue components (e.g., leaflets) are mounted to a frame or other component of the implant device. Inspection of the tissue mounting may be performed to confirm that no defects are present with respect to the tissue mounting. After tissue mounting, a commissure cover and/or one or more other components may further be connected or coupled to the device, which may generally obscure the visibility of certain features or aspects of the device. Therefore, inspection of such obscured features may generally be required to be performed prior to attachment of coverings. The inspection of a device may further be performed after a final assembly, after which a holder device or the like may be connected to the device, wherein after the holder device is connected to the device, certain aspects of the device may longer be visible or available for inspection. After connection of a holder device, additional inspection may be performed. In addition to the aforementioned inspections, certain other intermediate inspections may be performed in some implementations.

Manual visual inspection of the devices by human inspectors may further incorporate the use of certain probing or manipulation instruments or tools, which may be used to manipulate tissue or other components (e.g., leaflets of a prosthetic heart valve) for inspection thereof. For example, with respect to heart valve devices, visual inspection of the rim or interface between the biological leaflet tissue and the sewing ring may require the use of a tool to separate the tissue from the ring for inspection of the coupling thereof and/or associated components. Such tools may be generally rigid and have certain features for prying or leveraging between device components, which may be used to open the spacing between the tissue and/or other components to some degree to provide visibility of certain aspects and features of the device. In addition, a caliper tool, or other measurement instrument tool, may be used to assist in the determination of certain parameter measurements associated with the device during inspection.

A heart valve device may be inspected to determine whether delamination is present with respect to biological leaflet tissue of the device. One or more inspection tools can be used to confirm or disprove the presence of delamination in the tissue. Generally, delamination may represent a condition in which one or more layers of biological tissue that make up a valve leaflet or other component may become at least partially loosened are separated from one or more other layers thereof. Occurrence of delamination may result in the weakening or damage of the tissue, and therefore the presence of delamination may represent a parameter of inspection that may serve as a basis of a failure determination. The use of rigid tools as described above in inspecting implant devices can result in damage to the tissue or other components of the device in some situations. For example, sharp or rigid features of the tool(s) may tear or indent one or more portions or components of the device due to operator error and/or sensitivity of device components.

In some implementations, manual inspection of medical implant devices may be assisted through the use of one or more robotics or automation devices and/or cameras or imaging devices. Such devices may at least partially reduce the burden on the human inspector in inspecting the device. However, manipulation of devices by robotic or other automation tools may create a risk of damage by such devices to sensitive components of the device being inspected.

As described above, disadvantages relating to time, cost, and/or infliction of damage on inspected devices associated with manual human inspection and/or robotic-/automation-device-assisted inspection thereof may make such inspection processes and systems undesirable in some situations. For example, in addition to the relatively excessive time that may be associated with certain manual human inspection, manipulation of, for example, biological tissue of an implant device to inspect wedges or features thereof for delamination or other conditions may result in an increased risk of damage to the valve device through manipulation of the tissue or other components.

Device Inspection/Evaluation Using Imaging

Certain embodiments disclosed herein provide for improved inspection of prosthetic heart valves and other medical devices or apparatuses, wherein implementation of such embodiments may involve reduced or eliminated need for manual inspection by a human inspector. In some implementations, embodiments of the present disclosure utilize imaging devices and/or data, such as three-dimensional (3D) computed tomography (CT), magnetic resonance imaging (MRI), molecular imaging, and/or other imaging devices and/or data, to inspect medical implant devices, such as prosthetic heart valves and/or annuloplasty rings, wherein such imaging data may be processed to generate a pass/fail determination, or some other determination or decision. In some embodiments, pass/fail determinations may be based at least in part on the analysis of data relating to a large number of previously-inspected reference devices or products and associated imaging data, such reference devices being similar in one or more respects to the present target device under inspection, wherein correlations between features or characteristics of such imaging data of the plurality of previously-inspected reference devices and failure determinations are determined based on outcomes of inspections of such reference devices. In some embodiments, such previous inspection may have been performed at least in part by one or more current, trained inspectors. The determination of correlations between imaging data features and inspection outcomes may be part of a machine learning process or mechanism, as described in detail below. The machine learning process may be implemented or utilized by an inspection decision engine for the purpose of performing imaging-based inspection of devices in accordance with aspects of the present disclosure. The machine learning process may be enhanced through the input and/or use of inspection results that are generated by sampling and/or manual inspection. Such sampling and/or manual inspection input may provide a learning element for the machine learning process.

Figure 5:
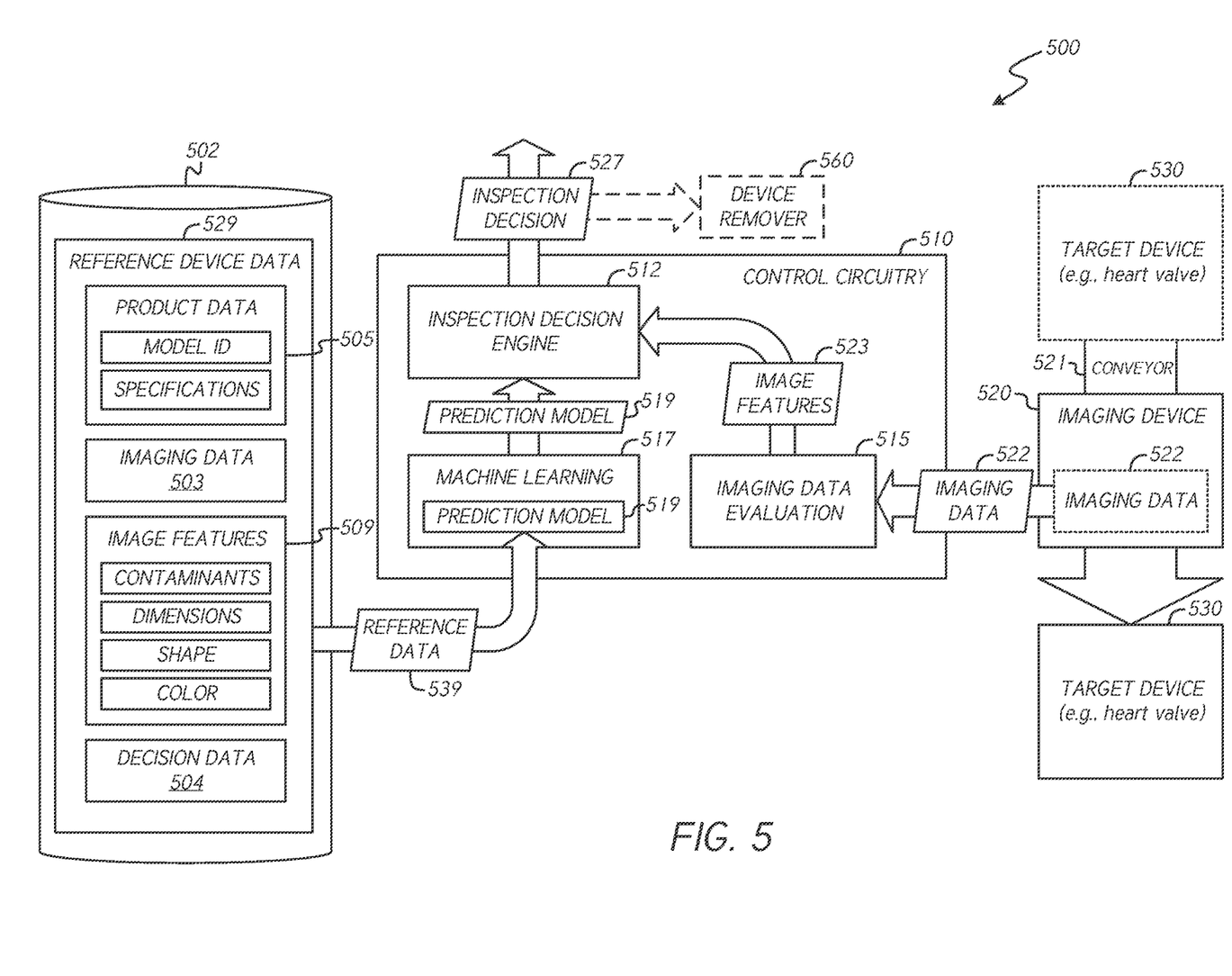
FIG. 5 illustrates an imaging-based inspection system in accordance with one or more embodiments.

FIG. 5 illustrates an imaging-based inspection system 500 in accordance with one or more embodiments. The system includes an imaging device 520, which is used to generate imaging data relating to a target device 530, such as a prosthetic heart valve device, as described in detail above. Although a single imaging device 520 is illustrated, it should be understood that any number of imaging devices and/or any combination of imaging device technologies may be implemented in the system 500. Therefore, the imaging device 520 should be understood to represent any number of imaging devices and/or type(s) of imaging device technologies. The target device 530 (e.g., prosthetic heart valve) may be manually placed in the imaging device 520 for imaging thereof, or may be fed into the imaging device 520 by a conveyor belt or mechanism 521. The imaging data 522 generated by the imaging device 520 and associated with the target device 530 is provided to certain control circuitry 510 of the system 500, which may be configured to perform certain inspection-related functionality as described herein.

The control circuitry 510 may comprise any number of hardware and/or software or firmware components. For example, the control circuitry 510 may include one or more application specific integrated circuits (ASICs), field-programmable gate arrays (FPGAs), circuits, digital logic circuits, analog circuits, a combination of discrete circuits, gates, or any other type of hardware or combination thereof. In addition, or alternatively, the control circuitry 510 may comprise one or more processors or processor circuitry, and/or instructions executable with by one or more processors or processor circuitry to implement one or more of the features of the control circuitry 510. The control circuitry 510 can take the form of processing circuitry, a microprocessor or processor, and/or a computer-readable medium that stores computer-readable program code (e.g., software or firmware) executable by the processing circuitry (e.g., microprocessor), and/or one or more logic gates, switches, application specific integrated circuits (ASICs), programmable logic controllers, or embedded microcontrollers.

The control circuitry 510 is a component, or module configured, to generate inspection decisions 527 for imaged target devices (e.g., prosthetic implant devices). The control circuitry 510 includes machine learning circuitry 517 configured to generate an inspection prediction model 519 for evaluating/inspecting imaging data (e.g., imaging data 522). The control circuitry 510 further comprises imaging data evaluation circuitry 515 configured to evaluate and/or parse imaging data to identify certain features and/or characteristics thereof that are applicable to failure determination, and may be reflected in the inspection prediction model 519.

The control circuitry 510 further comprises inspection decision engine circuitry 512, which is configured to make inspection/failure determinations based on the imaging data 522 and/or the image features 523, which may be provided as output from the imaging data evaluation circuitry 515. Although the diagram of FIG. 5 illustrates the decision engine circuitry 512, the machine learning circuitry 517, and the imaging data evaluation circuitry 515 as separate functional components, it should be understood that such components may be part of a single computing device, or may be combined in some way in some embodiments, or the functions thereof may be divided into additional functional and/or hardware units not shown in FIG. 5. Furthermore, although the decision engine circuitry 512, the machine learning circuitry 517, and the imaging data evaluation circuitry 515 are illustrated as part of the control circuitry 510, it should be understood that such functional units/circuitry may be distributed in any manner, and one or more components of the control circuitry 510 may be part of a separate and/or remote system with respect to one or more other components of the control circuitry 510. As used herein, one or any combination of the control circuitry 510, the decision engine circuitry 512, the machine learning circuitry 517, the imaging data evaluation circuitry 515, the datastore 502, and/or the imaging device 520 can be referred to as "control circuitry."

As referenced above, in some embodiments, the present disclosure provides for the use of scanning/imaging instrumentation to generate imaging data for target implant devices at one or more stages of the manufacturing process. For example, as shown in FIG. 5, the imaging device 520 may be configured to implement electromagnetic or other imaging technology to generate imaging data 522 for a target device 530 (e.g., medical implant device). In some embodiments, the imaging device 520 works in connection with a conveyance system 521, such as a conveyor belt, or the like, which may be configured to feed the medical implant device 530 through a scanning region or passage of the imaging device 520. Alternatively, an operator may manually place the target device 530 in the scanning area of the imaging device 520.

The imaging device 520 may incorporate any suitable or desirable imaging technology. Furthermore, the imaging device 520 may advantageously provide sufficient resolution and/or detail for identifying particles/contaminants between certain components of the target device 530. For example, with respect to embodiments relating to the inspection of prosthetic heart valve devices, the imaging device 520 may advantageously provide sufficient resolution to identify particles or other contaminants disposed between components of the heart valve device, such as between a tissue portion (e.g. valve leaflet) and a sewing/sealing ring structure, or other component(s). Furthermore, the imaging device 520 may further be configured to provide imaging data that can indicate positioning of sutures executed in the target device, which may be used to determine whether such sutures are in a correct position, or whether they have been mis-stitched.

The imaging device 520 may be configured to implement one or more of various imaging techniques known by those having ordinary skill in the art that provide for direct or indirect imaging of a structure. For example, in some embodiments, the imaging device 520 is configured to implement either two-dimensional or three-dimensional computed tomography (CT), or Computed Axial Tomography (CAT) scanning, which generally involves the use of X-rays from multiple different directions. CT scanning can involve utilization of certain control circuitry to performs a numerical integral calculation on measured X-ray series to estimate how much of an X-ray beam is absorbed in certain volumes of the target device being scanned. The imaging data generated in CT-type embodiments of the imaging device 520 may comprise one or more cross-sectional images of the target device.

In some embodiments, the imaging device 520 is configured to implement diffuse optical imaging (DOI), or diffuse optical tomography (DOT), which may generally involve the use of near infrared light to generate images of the target device. In such embodiments, the imaging device 520 may be configured to measure optical absorption in regions of the target device. In some embodiments, the imaging device 520 is configured to implement magnetic resonance imaging (MRI), which may generally involve the use of magnetic fields and radio waves to produce high quality two- or three-dimensional images of a target device.

In some embodiments, the imaging device 520 is configured to implement millimeter wave imaging, which may generally involve the use of millimeter waves transmitted from multiple antennas simultaneously as they rotate around a target device. The wave energy reflected back from the components of the target device on the body can be used to construct a three-dimensional image. Alternatively, or additionally, the imaging device 520 can be configured to implement backscatter X-ray technology, which may involve the transmission of X-ray radiation through the target device and detecting the radiation that reflects back from the target device. Other types of active and/or passive imaging technology may also be implemented by the imaging device 520. In some embodiments, the imaging device 520 utilizes ultrasound technology, which involves the use of sound waves generated at relatively high frequencies (e.g., between about 1-10 MHz) and measuring reflected sound waves to produce the imaging data.

As reference above, the imaging device 520 may implement, or operate in cooperation with, a conveyor device 521 (e.g., tunnel), or the like, to feed implant devices therethrough. The imaging data 522 generated of the medical implant device 530 may be interpreted by the control circuitry 510 substantially automatically and/or immediately, or may be evaluated by a trained human inspector. The imaging device 520 may advantageously be configured to provide cross-sectional image(s), or other image data, of the target device 530 without the need to rotate or otherwise reposition the device 530 during scanning. For example, in some embodiments, the imaging device 520 comprises rotating or otherwise moving imaging components configured to be rotated or otherwise move about the target device. Using an imaging device 520 as an alternative to manual inspection by an operator may allow for the inspection of the implant device 530 without the use of device manipulation tools or instruments as described above, which may cause damage to implant devices in some situations. In some examples, the target device can be rotated and/or translated (for example, on a conveyor belt or by a robotic arm) within an imaging field (for example, under X-ray illumination, or within a millimeter antenna array).

Although described generally herein in the context of scanning of individual medical implant devices, it should be understood that in some embodiments, the imaging device 520 may be used to scan a plurality of implant devices simultaneously in a batch, wherein the control circuitry 510 may be configured to parse or decipher imaging data from the batch of scanned devices to generate imaging information and/or features relating to each of the respective scanned devices. In some embodiments, the system 500 includes a device remover mechanism 560, which may be designed to remove a rejected product or device from a process flow that has been determined by the inspection decision engine 512 of the control circuitry 510 to meet certain failure criteria based on the inspection prediction model 519. For example, the device remover component 560 may comprise one or more robotic arms or components configured to draw or push the scanned medical device 530 from a conveyor belt or other component of the system 500.

In some embodiments, when the control circuitry 510 makes a failure decision with respect to a scanned target device, processes in accordance with the present disclosure may involve follow-up inspection by a trained human inspector to confirm rejection of the scanned device prior to disposal thereof.

As referenced above, the control circuitry 510 may comprise imaging data evaluation circuitry 515, which may be configured to analyze the imaging data 522 to identify certain features or characteristics thereof. For example, the imaging data evaluation circuitry 515 may be configured to generate image features data 523 indicating the presence of particulates or other contaminants, colors or shadows/shades in one or more components or regions, shape information, and/or dimensional information with respect to one or more components of the target device 530. In some embodiments, weight may be derived from imaging data characteristics, or alternatively may be measured using a scale or other weight-measuring mechanism of the imaging device 520. In some embodiments, dimensional information may be derived from the imaging data by locating or identifying one or more markers or other identifiers of the target device.

As referenced above, the control circuitry 510 may comprise machine learning circuitry 517, which may be configured to generate an inspection prediction model 519 based on analysis of certain reference device data 529. For example, the reference device data 529 may comprise imaging data 503, image features data 509 and/or decision data 504 relating to a set of previously-inspected and imaged reference devices (e.g., heart valve implant devices). The imaging data 503, the image features data 509, and the decision data 504 may be maintained in one or more data storage devices, referred to herein as a datastore 502. The imaging data 503 may include image data of a plurality of previously-scanned devices (not shown). The imaging data 503 may include the actual images generated by an imaging device (e.g., the imaging device 520), whereas the image features data 509 may include certain identified image parameters or characteristics (e.g., data indicating contaminant presence and/or location, colors, weights, dimensions, etc.) relating to the actual imaging data 503. Although FIG. 5 shows both the imaging data 503 and the image features data 509, the system 500 may include only one of the imaging data 503 and the image features data 509, or any combination of portions thereof. The decision data 504 may include data indicating actual inspection outcomes derived from human inspection of the reference devices, as associated with the respective reference devices. The datastore 502 may further store product data 505, which may include identifiers or other data associated with the type(s) of the reference devices.

An initial or early stage of a machine learning process for generating the inspection prediction model 519 may involve analyzing the imaging data 503, the image features data 509, and/or the decision data 504 relating to the reference device. The machine learning circuitry 517 (and/or other component (s) of the control circuitry 510) may determine connections with respect to the devices of the reference batch that ultimately failed manual/trained inspection compared to certain characteristics or features of imaging data associated therewith, such as device model, size, dimensional information, and/or other parameters. Such features may be provided in the image features data 509. The machine learning circuitry 517 may generate the prediction model 519 for predicting pass/fail decisions or determinations based on the evaluated imaging data 503, image features data 509, and/or decision data 504 of the reference device data 529. In some implementations, the generated inspection prediction model 519 may be validated against an additional batch of reference devices that are subsequently manually inspected to confirm accuracy of the prediction model.

Although the machine learning circuitry 517 is illustrated in proximity to the decision engine 512 and imaging data evaluation circuitry 515, it should be understood that such components may be distributed among any number of devices at any number of local or remote physical locations. Furthermore, the functionalities of each of the components of the control circuitry 510 may be performed by their respective functional components, or by any other component of the system 500, at different times. For example, the machine learning circuitry 517 may generate the inspection prediction model 519 temporally before, even significantly earlier than, the decision engine circuitry generates a failure determination with respect to the target device 530.

Inspection decision generation based on imaging data in accordance with embodiments of the present disclosure may provide for expedited and/or less labor-intensive inspection of medical implant devices. Image scanning devices and/or systems may therefore be used together with other information from relatively large data sets (e.g., reference inspection devices/data) that have been analyzed computationally to reveal correlations and/or associations between device failure and various parameters or characteristics of the device at one or more manufacturing stages.

In some implementations, imaging data generated by the imaging device 520 may be used for assisting a human inspector in visually inspecting the target device 530. That is, rather than the decision engine 512 of the control circuitry 510 providing a final inspection decision with respect to the target device 530, in some embodiments, a human inspector may inspect the imaging data 522 and/or image features data 523 to make a pass/fail determination for the target device 530. By providing imaging data 522 for inspection by the inspector, such processes may advantageously allow for the human inspector to make a pass/fail determination for the target device 530 without the need for manual manipulation of the target device 530 by the inspector. That is, rather than engaging in a cumbersome manual inspection processes, as described above, the inspector may rather interpret imaging data alone, or in addition to visual inspection of the target device itself. The imaging data 522 may further serve to aid a manual assembler or inspector, thereby potentially reducing the need for inspectors.

The imaging data 521 may provide sufficient detail for identifying particles that may be undesirably disposed or trapped in one or more components of the target device 530. For example, such particles may create certain shadows or other visually-identifiable features that may be identifiable by the imaging data evaluation circuitry 515. Using certain imaging technology, the imaging data 522 may further allow for visual identification of defects and various metal components of the medical implant device 530, such as metal frames, bands, or the like, as described in detail above. For example, certain metal components may be welded together or otherwise joined or coupled according to certain implant device manufacturing processes. The imaging data 522 may therefore advantageously indicate where metal components are not properly closed or coupled, or where undesirable openings/gaps are present therein, for example, voids, cracks, and defects.

Furthermore, the imaging data 522 may advantageously allow for identification of positioning and/or other features of sutures executed or disposed in the target device 530. For example, the imaging data 522 may indicate whether sutures are in the appropriate or desired positions, whether certain sutures are omitted or extra sutures are present, whether the correct type of suture was used, and/or whether the correct suturing pattern was used. In some implementations, the target device 530 is sutured using radiopaque sutures, which may be visible under fluoroscopy or using various types of electromagnetic radiation imaging. Alternatively, for other types of imaging technologies, sutures and/or other components of the implant device may comprise material that is designed to be visible using such imaging technology. For example, such materials may be configured to reflect soundwaves, or the like. In embodiments relating to heart valves or other medical implant devices as the target device(s), the characteristics of the biological tissue of the medical implant devices may be distinguishable from plastic and/or other components according to their material characteristics, such that the imaging data 522 relatively clearly presents the distinct elements comprised of different materials.

In some embodiments, the pass/fail determination with respect to the target device 530 may be based at least in part on an overlay of a plurality of different images. Such images may be generated using the same imaging technology, or may comprise images from multiple different imaging technologies. In some embodiments, the target device 530 is configured with one or more markers or other identifiers, which are visibly identifiable at least in part under imaging according to the technology of the imaging device 520. Therefore, such markers or identifiers may be captured or indicated in the imaging data 521. Radiopaque, or other markers visible under imaging, may be particularly useful where the target device 530 is not perfectly symmetric with respect to one or more cross-sections or planes. In some embodiments, the imaging data 522 and/or imaging device 520 are configured to provide imaging detail for measurement of dimensions of the target device 530 to the tens of millimeters, or millimeters level of granularity. Generally, the lower the resolution of the imaging device 520 and/or imaging data 522, the less accurate the prediction decision of the decision engine 512.

With respect to heart valve devices, the imaging data 503 and/or imaging data 522 may comprise information identifying or relating to the presence of particles, and/or suturing/sewing patterns, which may be identified based on their different material characteristics relative to the surrounding tissue and/or materials. For example, the image features 523 and/or image features 509 may identify thread counts and/or whether enough associated meshes have been used. That is, with respect to certain heart valve sewing processes, openhole fabric may be weaved into a grid-like finish or arrangement to produce mesh-type weaves (e.g., "meshes"), wherein sewing needles are threaded every x meshes. In some heart valve inspection implementations, the image features 523 and/or image features 509 may be associated with a manufacturing stage after a commissure cover as described in detail above has been attached. The reference device data 520 maintained in the datastore 502 may further comprise product data 505, which may include other data associated with the reference devices, such as product IDs, or the like.

In some embodiments, the reference device data 529 includes imaging data, decision data, and/or product data for thousands of reference devices, or more, which have been inspected at least in part by trained human inspectors. The machine learning circuitry 517 may be configured to link the identified image features 509 of the imaging data 503 and/or product data 505 with outcomes embodied in the decision data 504 for the respective inspected reference devices. Once the machine learning circuitry 517 has generated the inspection (e.g., pass/fail) prediction model 519, the decision engine circuitry 512 may be able to use the model 519 to determine if a given imaged target device (e.g., medical implant device) fits certain criteria of the model that is associated with a failure projection. Therefore, as long as the imaging data 522 captured by the imaging device 520 is sufficient to identify certain features/characteristics, artifacts, particulates, or the like that serve as a basis for the prediction model 519, the decision engine 512 may be able to make a product rejection determination.

The imaging features 503 and/or image features 523 may comprise any type of image data derivable from imaging data of a target device. For example, as illustrated, the image features 509 (and/or image features 523) may comprise dimensions data, which may provide measurement values for various dimensions of the relevant target device. Such dimensions may be linked to pass/fail determinations, as captured in the decision data 504. The dimension data may be related to any suitable or desirable dimension(s) of the target device, such as, with respect to heart valve devices, dimensions relating to openings or gaps between the valve leaflets. The dimension data may further indicate heights or other dimensions of leaflets of a heart valve device and/or relative vertical and/or horizontal offsets between the valve leaflets. Additional dimension data may comprise frame size and/or diameter measurements, commissure post heights and/or angles, or the like.

The image features 509 (and/or image features 523) may further comprise shape data, which may include indications or values indicating a shape of one or more portions or components of a heart valve or other target device. For example, the shape data may indicate whether a valve has a desired round shape, or is deformed undesirably. The image features 509 (and/or image features 523) may further comprise color data, which may indicate colors of one or more components or regions of the relevant target device. For example, color markers associated with heart valve leaflets may indicate that tissue of the valve leaflets is undesirably dehydrated or brittle. Such color markers or differences captured in the color data may be correlated with the decision data 504 to indicate the significance of certain colored components or regions thereof with respect to failure decisions. With respect to valve leaflets, discoloration may be due at least in part to delamination, wherein there may be air trapped or disposed undesirably between tissue layers, which may be visually apparent in the imaging data. The product data 505 may comprise model ID/number data, or other product identifier information, as well as product size data, or other specifications.

The prediction model 519 generated by the machine learning circuitry 517 may combine a plurality of image features in making failure decisions. For example, a failure decision may be based on a combination of features, such as the presence of one or more colors in one or more components or regions, combined with the presence of certain spots or particulates/contaminants, as well as a discontinuity or defect in a component, such as frame welding or form defect. For example, where only one of a plurality of combined parameters is present for a particular target device, while other required parameters are absent, the device may nevertheless not be rejected according to the model 519. The machine learning circuitry 517 may be configured to determine the dimensional values and/or other parameters that serve as the threshold for failure determinations. In some embodiments, the model 519 comprises or represents a three-dimensional complex curve. The model 519 advantageously describes the correlation between the various parameters/features that are identified as being statistically significant with respect to outcomes. The machine learning circuitry 517 may be configured to disregard parameters or features that are determined to not have a substantial or significant bearing on device rejection/failure outcomes. In some embodiments, the model 519 provides a polynomial equation that fits the reference device data maintained in the reference data datastore 502. For example, the polynomial model or equation may include one or more variables that correspond to, or represent, image features or other imaging-data-based criteria.

In some embodiments, the imaging data 522 projects the imaged target device on a visual measurement scale or coordinate grid, which provides additional information with respect to dimensions or other features of the imaged target device when the image is superimposed on the grid. Using a grid or other visual measurement representation may advantageously assist in making the visual features of the imaging data 522 quantifiable to a reader thereof.

Sanitation of Target Devices Using Imaging Device

With respect to heart valve and other medical implant devices, unsterile conditions thereof can pose serious health risks. Therefore, in some embodiments, the imaging device 520 that is used to generate imaging data for the target device 530 may also be configured to perform sterilization functionality to at least partially sterilize the target device 530. Generally, sterilization in accordance with embodiments of the present disclosure may involve eliminating, removing, killing, or deactivating undesirable biological agents (e.g., fungi, bacteria, viruses, spore forms, prions, and the like) present in a target device, or surface, volume, fluid, compound, or component thereof.

Sterilization may be achieved in the system 500 using electron beams, chemical agents (e.g., ethylene oxide, or nitric oxide), electromagnetic radiation (e.g., X-rays, gamma rays, ultraviolet (UV) light), or other technology. The imaging device 520 may advantageously use the same radiation technology used for device imaging to sterilize target devices. In some embodiments, a different technology is used for sanitation than for imaging. Sanitation may be performed by the imaging device 520 simultaneously with imaging of the target device, or prior to, or subsequent to imaging.

Imaging-Based Inspection Processes

Figure 6:
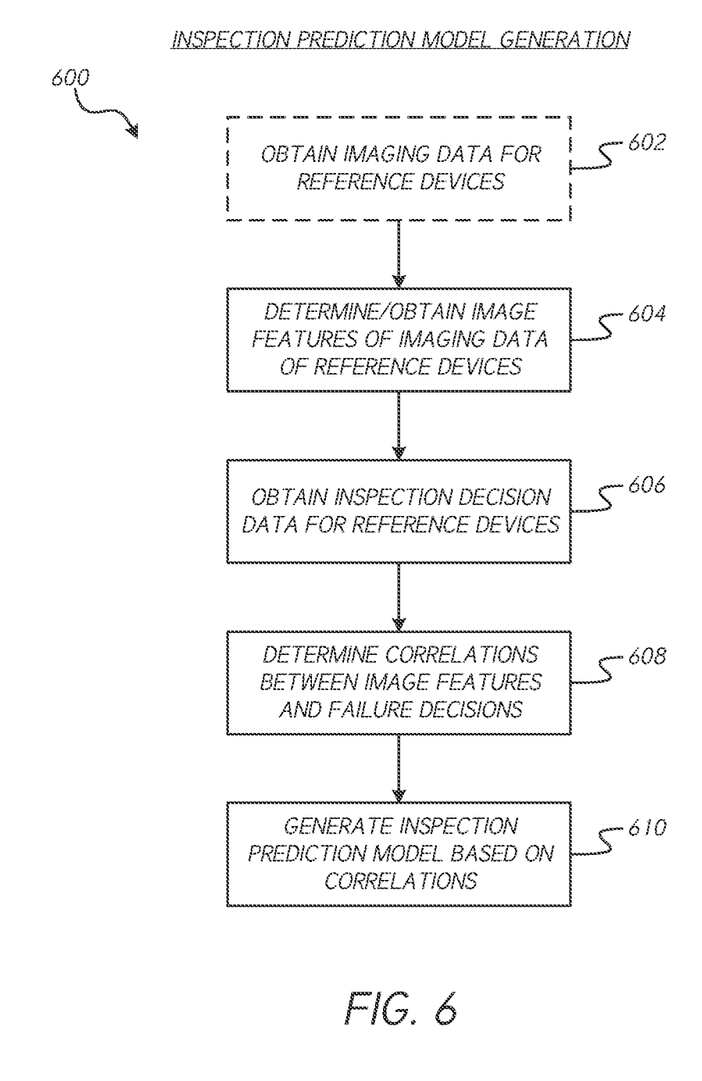
FIG. 6 is a flow diagram illustrating a process for generating an inspection prediction model in accordance with one or more embodiments.

FIG. 6 is a flow diagram illustrating a process 600 for generating an inspection prediction model in accordance with one or more embodiments. The process 600 may be performed at least in part by control circuitry of a device inspection system or device in accordance with embodiments of the present disclosure. With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any given method or process, and the illustrated/described methods and processes may include additional operations or steps not explicitly illustrated or described.

At block 602, the process 600 involves obtaining image data for a set of reference devices. For example, the image data may comprise images for a substantial number of previously-inspected devices, such as heart valve implant devices or the like.

At block 604, the process 600 involves determining image features of the imaging data of the reference devices. For example, various dimensions, colors, shapes, contaminants and/or other features of the reference device imaging data may be determined and/or identified. For example, the process 600 may involve accessing imaging data and/or image feature data corresponding to a plurality of imaged reference devices, which may be maintained in a datastore comprising one or more data storage devices. Such imaging data and/or image feature data may have been generated for the purpose of calibration of an inspection prediction engine. In some embodiments, determining the image features involves accessing stored image feature data in a datastore. In some embodiments, determining the image features involves generating the image features based at least in part on the imaging data. In some embodiments, the process 600 does not involve obtaining the imaging data at block 602, but rather merely involves obtaining the image feature data. The image feature data may comprise any number of features, such as various dimensions, colors, weights, sizes, shapes, or the like of the plurality of reference devices (e.g., medical implant devices).

At block 606, the process 600 involves obtaining inspection decision data for the reference devices. For example, the inspection decision data may comprise data indicating inspection outcomes relating to the reference devices, wherein such inspection outcomes can be determined by trained human inspectors, or through some other means.

At block 608, the process 600 involves determining correlations between image features of the reference device imaging data and failure decisions of the respective devices from the inspection decision data. As described above, in some embodiments, processes for generating pass/fail decisions for device (e.g., medical implant device) inspection may involve machine learning to determine correlations between imaging features or characteristics and pass/fail determinations.

At block 610, the process 600 involves generating an inspection prediction model or criteria based on the determined correlations between the image features and the failure decisions of the reference inspection decision data. The prediction model may be used to evaluate image data of subsequently-imaged target devices. For example, the process 600 may involve analyzing the imaging data and/or image features data, vis-à-vis the reference inspection decision data to determine correlations between the image features associated with the imaging data and pass and/or fail decision outcomes of the reference inspection decision data. The inspection prediction model may be generated without knowledge of the relevance or significance of the various image features, outside of the correlation between such features and the decisions made with respect to their associated reference devices.

Figure 7:
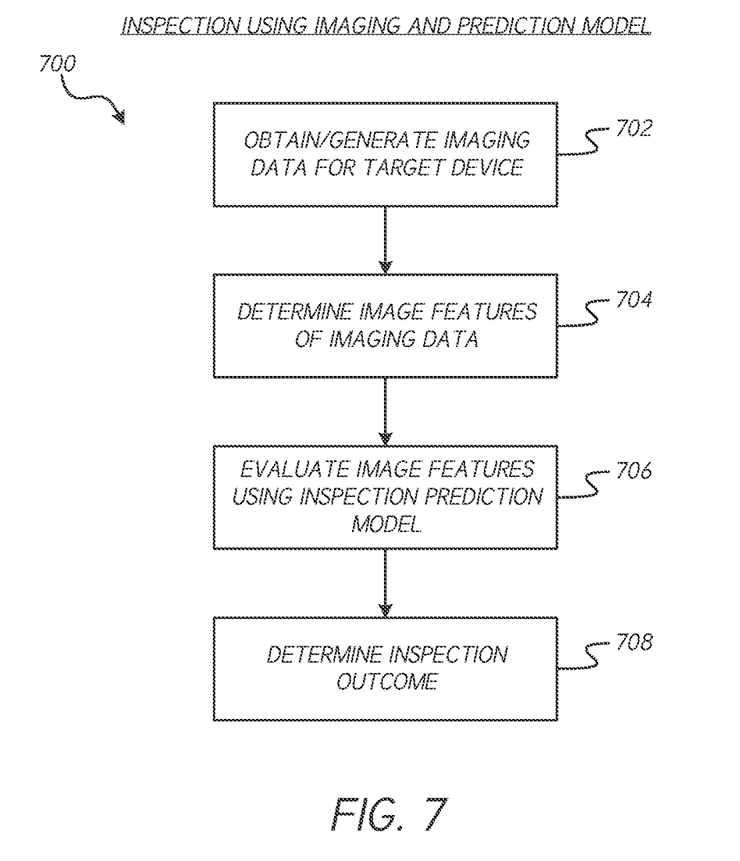
FIG. 7 is a flow diagram illustrating a process for inspecting a device in accordance with one or more embodiments.

FIG. 7 is a flow diagram illustrating a process 700 for inspecting a device in accordance with one or more embodiments. The process 700 may be performed at least in part by control circuitry of a device inspection system or device in accordance with embodiments of the present disclosure.

At block 702, the process 700 involves obtaining and/or generating imaging data for a target device. For example, the imaging data may be generated using an imaging device, such as a radiation imaging device, as described in detail herein.

At block 704, the process 700 involves determining certain image features of the imaging data of the target device. For example, certain color, shape, weight, dimension, and/or other feature(s) of the imaging data may be identified. In addition, or alternatively, certain other features may be evaluated or derived from imaging data, such as the presence of particulates or other contaminants, or the like. The image features may be correlated (e.g., determined to be correlated) with failure decisions of previously-inspected reference devices, and/or may be relevant to known inspection prediction model or criteria.

At block 706, the process 700 involves evaluating the image features of the target device using an inspection prediction model or criteria. For example, the inspection prediction model may be used to identify features of the imaging data of the target device that correspond to failure criteria of the inspection prediction model. At block 708, the process 700 involves determining an inspection outcome based on the inspection prediction model. For example, an inspection prediction model may be used to determine a failure decision, which may result in rejection and/or disposal of the target device.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component, and another element or component as illustrated in the drawings. It will be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. An apparatus for inspecting a target device, the apparatus comprising:
    a data communication interface; and
    control circuitry configured to:
        train an image-based machine learning framework on prosthetic heart valve image data at least in part by:
            obtaining image feature data associated with a plurality of reference prosthetic heart valve devices;
            obtaining inspection decision data corresponding to the plurality of reference prosthetic heart valve devices, the inspection decision data including failure decision data;
            determining correlations between the failure decision data and the image feature data; and
            determining a failure prediction model based on the correlations;
        receive imaging data of a target prosthetic heart valve device using the data communication interface, the target prosthetic heart valve device comprising a sealing skirt sutured to a frame by a suturing line that follows an undulating shape of struts of the frame;
        identify suture features associated with the suturing line based at least in part on the imaging data;
        determine whether the suture features are correctly positioned based at least in part on the failure prediction model; and
        determine an inspection outcome based at least in part on the determination of whether the suture features are correctly positioned.

2. The apparatus of claim 1, wherein the imaging data comprises three-dimensional computed tomography imaging data.

3. The apparatus of claim 1, wherein the sealing skirt is wrapped around one or more frame struts.

4. The apparatus of claim 1, wherein:
    the inspection outcome is a failure determination; and
    the control circuitry is further configured to send a command to a device remover device to remove the target prosthetic heart valve device from a manufacturing process flow based on the failure determination.

5. A method of determining an inspection decision for a target device, the method comprising:
    training an image-based machine learning framework on prosthetic heart valve image data at least in part by:
        obtaining image feature data associated with a plurality of reference prosthetic heart valve devices;
        obtaining inspection decision data corresponding to the plurality of reference prosthetic heart valve devices, the inspection decision data including failure decision data; and
        generating a failure prediction model based on correlations between the failure decision data and the image feature data;
    obtaining imaging data for a target prosthetic heart valve device, the target prosthetic heart valve device comprising a sealing skirt sutured to a frame by a suturing line that follows an undulating shape of struts of the frame;
    determining positioning of the suturing line based on the imaging data;
    evaluating whether the suturing line is correctly positioned using the failure prediction model; and
    determining an inspection outcome associated with the target prosthetic heart valve device based on the evaluation.

6. The method of claim 5, wherein the imaging data comprises computed tomography imaging data.

7. The method of claim 5, wherein the image feature data includes one or more of contaminant presence data, dimensions data, color data, or shape data.

8. The method of claim 5, further comprising removing the target prosthetic heart valve device from a process flow based on the inspection outcome.

9. The apparatus of claim 4, wherein: the device remover device comprises one or more robotic arms configured to remove the target prosthetic heart valve device from a conveyor.

10. The apparatus of claim 1, wherein the control circuitry is further configured to determine:
a suturing pattern of the suturing line; and
determine a negative inspection outcome based on a determination that the suturing pattern is an incorrect suturing pattern.

11. The apparatus of claim 1, wherein the control circuitry is further configured to:
determine a suture type of the suturing line; and
determine a negative inspection outcome based on a determination that the suture type is an incorrect suture type.

12. The apparatus of claim 1, wherein:
the suturing line comprises echogenic suture material configured to reflect soundwaves; and
the image feature data is associated with a sonic imaging modality.

13. The method of claim 5, wherein said determining the inspection outcome involves:
determining a suturing pattern of the suturing line; and
determining a negative inspection outcome based on a determination that the suturing pattern is an incorrect suturing pattern.

14. The method of claim 5, wherein said determining the inspection outcome involves:
determining a suture type of the suturing line; and
determining a negative inspection outcome based on a determination that the suture type is an incorrect suture type.

15. The method of claim 5, wherein said obtaining the imaging data involves reflecting sound waves off of the suturing line, wherein the suturing line comprises echogenic suture material configured to reflect soundwaves.

16. The method of claim 8, wherein said removing the target device is implemented automatically using a robotic instrument.

\* \* \* \* \*